United States Patent [19]
Vreman et al.

[11] Patent Number: 5,383,469
[45] Date of Patent: Jan. 24, 1995

[54] NEONATAL HEMOLYSIS DETECTION USING END-TIDAL BREATH SAMPLER AND ANALYZER APPARATUS

[75] Inventors: Hendrik J. Vreman, Los Altos; David K. Stevenson, Palo Alto, both of Calif.

[73] Assignee: Board of Trustees of the Leland Stanford Junior University, Palo Alto, Calif.

[21] Appl. No.: 135,142

[22] Filed: Oct. 12, 1993

Related U.S. Application Data

[63] Continuation of Ser. No. 829,843, Jan. 31, 1992, abandoned.

[51] Int. Cl.⁶ .............................................. A61B 5/08
[52] U.S. Cl. .................................... 128/719; 128/724; 128/730; 73/23.3
[58] Field of Search ............... 128/716, 719, 725, 724, 128/727, 730; 73/23.3, 23.2; 364/413.02, 413.03

[56] References Cited

U.S. PATENT DOCUMENTS

| | | | |
|---|---|---|---|
| 3,910,261 | 10/1975 | Ragsdale et al. | 128/719 |
| 4,155,358 | 5/1979 | McAllister et al. | 128/146.6 |
| 4,220,162 | 9/1980 | Clark et al. | 128/724 |
| 4,248,245 | 2/1981 | Kempin | 128/719 |
| 4,485,822 | 12/1984 | O'Connor et al. | 128/719 |
| 4,777,963 | 10/1988 | McKenna | 128/724 |
| 4,831,024 | 5/1989 | Vreman et al. | 514/185 |
| 5,069,220 | 12/1991 | Casparie et al. | 128/719 |
| 5,069,222 | 12/1991 | McDonald, Jr. | 128/724 |
| 5,293,875 | 3/1994 | Stone | 128/719 |

FOREIGN PATENT DOCUMENTS 2575917 7/1986 France .............................. 128/724

OTHER PUBLICATIONS

Stevenson, "The Use of Metalloporphyrins for the Chemoprevention of Neonatal Jaundice," AJDC, vol. 143, Mar. 1989, pp. 353–356.
Weitz, "High Breath Pentane Concentrations During Acute Myocardial Infarction," The Lancet, vol. 337, Apr. 20, 1991, pp. 933–935.
Smith, "Neonatal Bilirubin Production Est. From End-Tidal CO Concentration," J. Ped. Gastro. & Nut., vol. 3, No. 1, '84, p. 77.
Smith, "Use of Noninvasive Tests to Predict Sig. Jaundice in Full-Term Inf: Prelim. Studies," Peds., vol. 75, No. 2, Feb. 1985.
Yeung, "Auto. End-Expiratory Air Sampling Device for Breath Hydrogen Test in Infants," Lancet, vol. 337, Jan. 12, 1991, pp. 90–93.
Operating Instructions-Syringe Pumps, Braintree Scientific, Inc. Jan. 18, 1991 6 Pages Author unknown.
Odyssey 2001 Application Note, Transducer Research, Inc., Dec. 18, 1990 Author unknown.

Primary Examiner—Stephen C. Pellegrino
Assistant Examiner—Guy V. Tucker
Attorney, Agent, or Firm—Townsend and Townsend Khourie and Crew

[57] ABSTRACT

Apparatus for use in a hospital nursery, clinic, or physician's office for the sampling and analysis of neonatal end-tidal breath for carbon monoxide as an indication of hemolysis and subsequent infant jaundice includes a syringe and plunger for collecting end-tidal breath, a pump for supporting the syringe and including drive means for incrementally withdrawing the plunger and collecting end tidal breath, and a controller for the pump including a thermistor positionable to respond to the temperature of exhaled breath and generating an electrical signal in response to thermistor temperature. A rate detector receives the signal and determines exhalation rate. The signal is delayed in response to exhalation rate and then utilized to energize the pump in incrementally withdrawing the plunger in collecting end tidal breath. The pump can also be used in analysis equipment which extracts the end tidal breath sample with a sensor receiving the sample and determining carbon monoxide content. Alternatively, separate pumps can be employed for the sample collection and for the sample analysis.

1 Claim, 1 Drawing Sheet

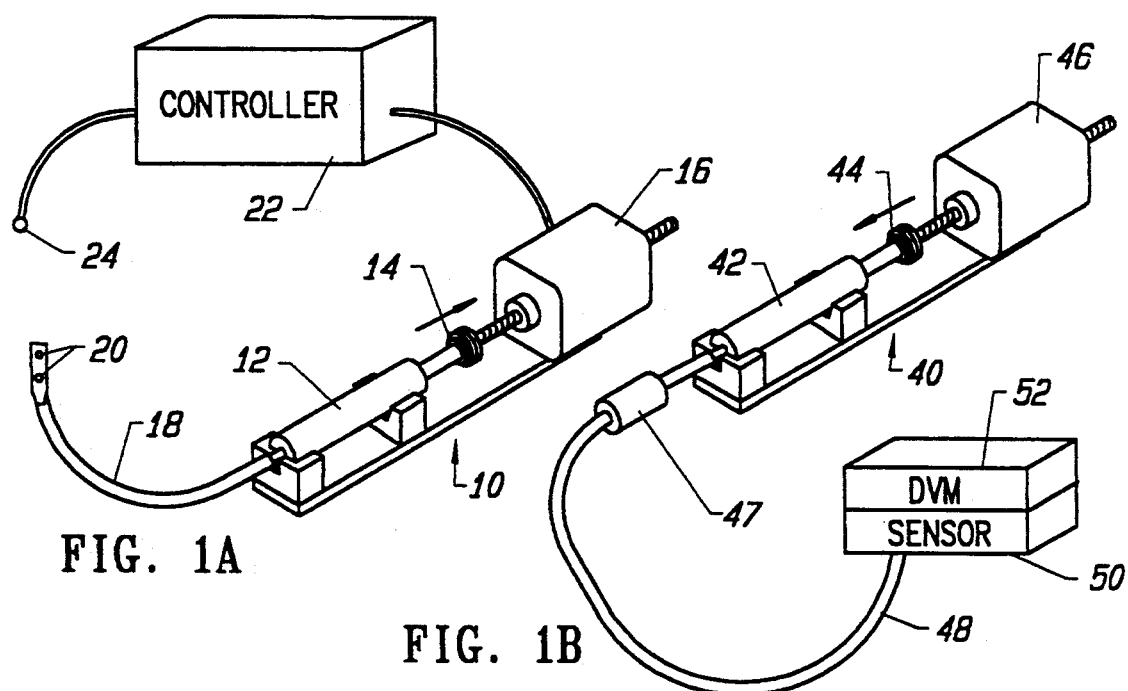
FIG. 1A
FIG. 1B
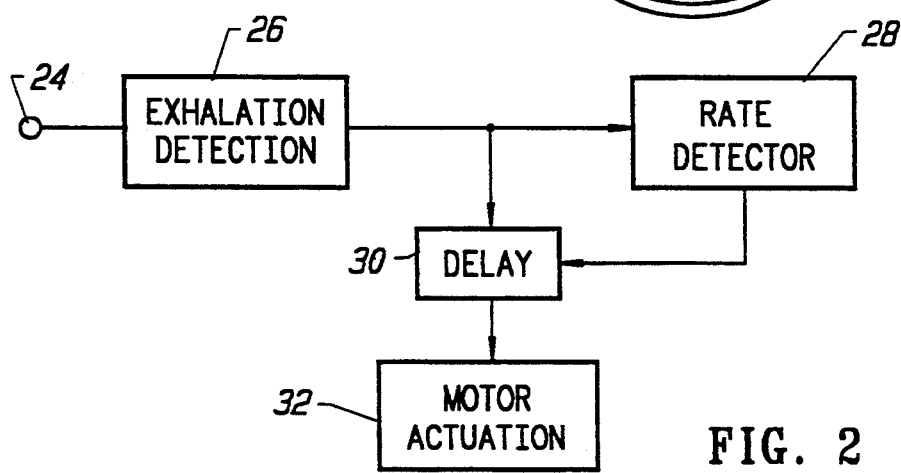
FIG. 2
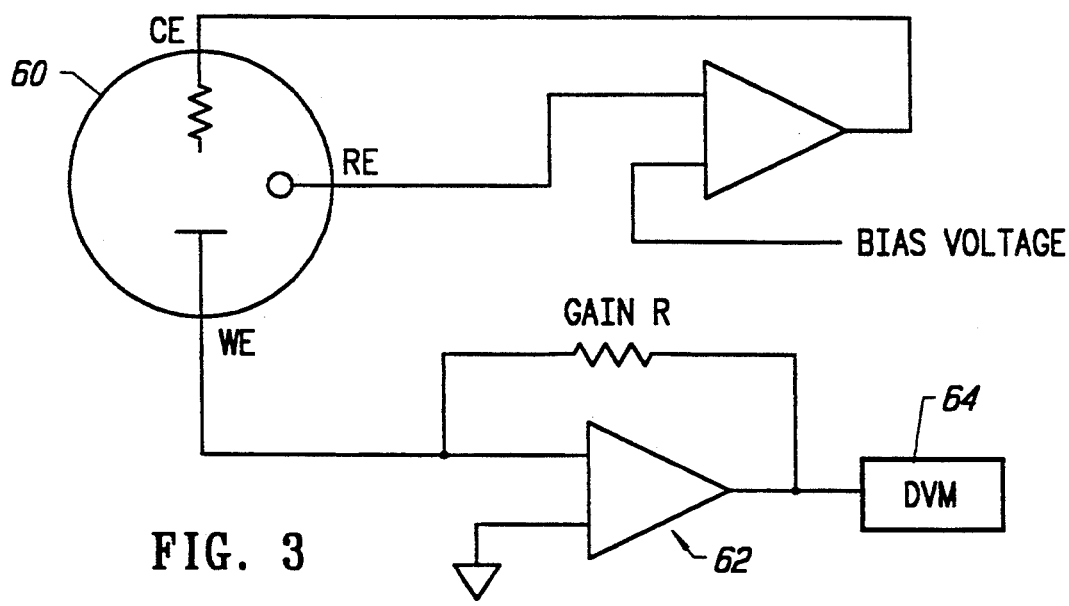
FIG. 3

NEONATAL HEMOLYSIS DETECTION USING END-TIDAL BREATH SAMPLER AND ANALYZER APPARATUS

This is a continuation of application Ser. No. 07/829,843, filed Jan. 31, 1992, now abandoned.

BACKGROUND OF THE INVENTION

This invention relates generally to the detection of hemolysis and subsequent development of neonatal jaundice, and more particularly the invention relates to improved apparatus for hospital nursery use in sampling and analyzing end tidal breath for carbon monoxide content as an indication of jaundice. The invention has further applications in the detection of other exhaled gasses.

Infant hemolysis leading to hyperbilirubinemia and jaundice is a significant clinical problem which results directly from increased bilirubin levels in the infant body. As discussed in U.S. Pat. No. 4,831,024 issued to Vreman and Stevenson for "Method to Prevent Neonatal Jaundice" the toxic cause of jaundice and treatment thereof are known. However, in the newborn, or neonate, the visible signs of the disorder usually manifest themselves several days after birth, often after the infant and mother have been discharged from the hospital.

A simple non-invasive test for hemolysis and subsequent jaundice is based on carbon monoxide analysis of end expiratory breath sample collected transnasally. As described by D. W. Smith, et al., Journal of Pediatric Gastroenterology and Nutrition (1985) 4: 38–44, samples of end-expiratory breath are collected by transnasal placement of a catheter into the posterior nasal pharynx. Expired gas is drawn manually by nursery personnel in small, less than 1 ml, increments at end expiration as determined by the infants chest wall movement. A syringe of sufficient size such as 12 cc is used to permit the collection of a total of approximately 10 ml of expired breath. Ambient air is also sampled, and the sampled measurements are corrected for the contribution of ambient CO which can vary in the range of 0.2–10 $\mu l/l$. The CO in the samples is then measured in a laboratory using gas chromatography.

C. Y. Yeung, et al. describe in the Lancet Volume 337: Jan. 12, 1991 pp. 90–93 apparatus for collecting end expiratory air samples. A hot wire sensor consisting of a set of seven tungsten hot wires is cooled by expired air flow which causes an imbalance in a Wheatstone bridge circuit. The bridge circuit sends a signal to a syringe driver controller which then collects an end expiratory air sample. A variable time switch can be set to delay the collection of samples. The air sample is then analyzed in a laboratory for hydrogen content to detect lactose malabsorption.

The present invention provides apparatus for use in a nursery, clinic, or physician's office for automatic sampling and analyzing end expiratory air without the requirement for laboratory analysis or highly trained personnel.

SUMMARY OF THE INVENTION

Accordingly, an object of the invention is improved apparatus for collecting and analyzing end expiratory air samples.

Still another object of the invention is improved end expiratory sensing, sampling, and analyzing apparatus which reduces hospital personnel time and expertise in obtaining and analyzing samples.

Another object of the invention is analyzing apparatus for breath samples which can be accommodated in a nursery, a clinic, or a physician's office.

A feature of the invention is the use of a thermistor sensor to detect the start of breath exhalation.

Another feature of the invention is the detection of a stable expiration rate before end tidal breath sampling is started.

Yet another feature of the invention is a variable delay in sample collection depending on exhalation rate.

Still another feature of the invention is a bidirectional syringe pump for sample collection and sample analysis.

Another feature of the invention is an analyzer including a pump for discharging air samples to a electrochemical sensor.

The invention and objects and features thereof will be more readily apparent from the following detailed description and appended claims when taken with the drawings.

BRIEF DESCRIPTION OF THE DRAWINGS

FIGS. 1A and 1B are perspective views of end tidal breath sampling apparatus and analysis apparatus, respectively, in accordance with one embodiment of the invention.

FIG. 2 is functional block diagram of the controller for the sampling pump in FIG. 1.

FIG. 3 is a functional block diagram of the analyzer pump and sensor in FIG. 1.

DETAILED DESCRIPTION OF THE ILLUSTRATIVE EMBODIMENTS

Referring now to the drawing, FIGS. 1A and 1B are an illustrative embodiment of neonatal end tidal sampler and analyzer in accordance with the invention. The sampler includes a pump 10 which supports a syringe 12 and plunger 14 with a motor 16 of the pump incrementally withdrawing the plunger in collecting end tidal breath. A suitable syringe pump is available from Braintree Scientific Incorporated of Braintree, Mass. which is preferably modified to include a battery powered DC motor. One end of a catheter 18 is connected to the syringe 12, and another end of the catheter with one or more openings 20 is inserted into the nostril of an infant for breath sample collection. Catheter 18 can have a diameter of 5 French and a length of 18–36 inches.

A controller 22 energizes the motor 16 of the pump in collecting the sample. The controller 22 is connected to a thermistor 24 which is positionable near the nostril of the infant for sensing the temperature of inhaled air and exhaled breath with the temperature dropping for inhaled air and rising for exhaled air. The temperature change of the thermistor causes a detectable change in resistance in the device. The controller 22 responds to the rise in temperature of thermistor 24 as indicating exhalation, and as illustrated in FIG. 2 provides a signal to a rate detector 28 for detecting the exhalation rate. In accordance with one feature of the invention the rate detector prevents the energization of the pump motor until the rate becomes uniform over a number of breaths. After the breathing rate has become uniform, the rate detector 28 activates a 50–250 millisecond delay of the exhalation signal at 30 so that the motor actuation 32 is delayed after the beginning of exhalation until near the end tidal breath.

In operation, inhalation and exhalation are determined by the derivative of the voltage change across the thermistor with a negative derivative indicating that exhalation is in progress. Two monostable timers are triggered by the derivative signals generated by a differentiator/comparator. For breath rates less than 40 breaths per minute, both monostable timers are timed out before the end of exhalation, two data flip-flops connected to the monostable timers remain reset, and a delay timer responsive to the flip-flops is set for a 250 millisecond delay. When the breath rate exceeds 40 breaths per minute but less than 80 breaths per minute, only one of the monostable timers will time out and one of the flip-flops will be set which changes the delay timer to 100 milliseconds. When the breath rate equals or exceeds 80 breaths per minute, neither monostable timer will time out, both flip-flops will be set, and the delay timer will be set for a 50 millisecond delay. The pump motor is then actuated after a delay of 250 milliseconds for a breath rate of less than 40 breaths per minute, 100 milliseconds for a breath rate of 40–80 breaths per second, and 50 milliseconds for a breath rate greater than 80 breaths per second. Changes in the set/reset states of the flip-flops are integrated as changes in the breathing rate, and pump actuation is inhibited until the flip-flop states remain stable for at least four breaths.

The end expiratory CO concentration reflects breath that comes from the deepest portions of the lung, and most accurately reflects alveolar levels of CO. Since the end expiratory portion of each breath, or end tidal breath, lasts only a fraction of a second and has a limited low volume, the breath sampler must collect many samples of the end tidal breath and save them in the syringe 12. The thermistor can be sterilized for re-use.

The pattern of respiration varies from infant to infant and from breath to breath. Therefore, the breath sampler must determine the respiratory rate of each infant and will not begin sampling until the respiratory rate has been stable for several breaths. If the respiratory rate is high, the motor is turned on just after the start of the expiration. If the respiratory rate is low, the maximum end tidal concentration of CO occurs later, and there is a longer delay until the pump motor is energized. If the respiratory rate again becomes unstable, the syringe pump will pause until the rate stabilizes.

Referring again to FIG. 1, a second pump 40 is provided in the nursery for receiving a syringe 42 filled with an end tidal or ambient air sample. The plunger 44 is driven into the syringe 42 by a drive motor 46 to expell the sample through a filter 47 and a catheter 48 to an electrochemical sensor 50 and digital voltmeter 52. The filter comprises a cylinder filled with activated carbon to trap interfering gasses in the sample. A cylinder having an inside diameter of approximately four mm and a length of 30 mm functions satisfactorily in trapping contaminants while passing CO after the first two cubic centimeters have been injected. Use of the filter improves the correlation between instruments. The sensor 50 can determine the carbon monoxide content of the sample by converting the carbon monoxide to carbon dioxide, which reaction creates an electron flow. The current from the electron flow is then converted to a voltage which is measured by the digital voltmeter 52 as an indication of carbon monoxide content.

A suitable sensor is manufactured by Transducer Research Incorporated of Naperville, Ill. As illustrated in FIG. 3, an amperometric gas sensor 60 consists of three electrodes immersed in a liquid electrolyte. The three electrodes are a reference electrode (RE), a counter electrode (CE), and a working electrode (WE). The working electrode is usually a catalytic metal such as platinum deposited on a membrane of porous Teflon. The CO gas being measured diffuses through the porous membrane and is oxidized in response to an electric potential on the working electrode. The transfer of electrons that accompanies the chemical reaction flows through the working electrode to an external circuit which constitutes the output of the sensor. The reference electrode serves the purpose of indicating the potential of the electrolyte and is normally protected from exposure to the sample gas so that its potential is always the same relative to the electrolyte. The current flowing through the working electrode is compensated by a current provided through the counter electrode of equal and opposite current flow. The signal current from the working electrode is converted to a voltage by the measuring circuit shown generally at 62 with the voltage being displayed by a digital voltmeter 64.

In operation, three end tidal breath samples are obtained for each infant and three ambient air samples are also obtained. The measured carbon monoxide in the expired end tidal breath sample must be reduced by the amount of carbon monoxide present in the inhaled ambient air.

The analyzer can be calibrated with a zero gas (i.e. no carbon monoxide or other interfering compounds present). The digital voltmeter read out is adjusted to zero for this gas. Then air, containing a known concentration of carbonmonoxide, (e.g. 10 parts per million) is analyzed and the digital voltmeter readout recorded. Approximately 1.00 volt d.c. corresponds to the 10 $\mu l/l$ gas. An infant without hemolysis will have 0.5–2.0 $\mu l/l$ carbon monoxide in end tidal breath (0.05–0.20 volts d.c.), and an infant suffering from hemolysis will have 2.00–8.00 $\mu l/l$ carbon monoxide (0.20–0.80 volts d.c.). Thus, the reading from the digital voltmeter 64 gives a direct measure of the carbon monoxide present in the end tidal sample, and after compensating for the ambient carbon monoxide, the susceptibility of an infant to excessive jaundice, which might not occur until 2–3 days later, is readily predicted. Conversely, an infant with a low risk of non-physiologic jaundice can be safely discharged early from the hospital.

The invention permits the automatic collection of more accurate samples and without the continuous intervention of hospital personnel. The end tidal samples can be readily collected and analyzed in the nursery without the requirement for complicated and expensive high technology equipment needing highly trained personnel. Further, removal of the samples to a distant laboratory for example is not required. A single pump can be employed for both the sample collection and the sample analysis but with a concurrent delay in the obtaining and analyzing of samples.

While the invention has been described with reference to a specific embodiment, the description is illustrative of the invention and is not to be construed as limiting the invention. For example, the apparatus can be used in collecting and analyzing other gases such as hydrogen. Further, the apparatus can be readily employed in a clinic or physician's office without the requirement for laboratory analysis of the sampled gas. Thus, various modifications and applications may occur to those skilled in the art without departing from the true spirit and scope of the invention as defined by the appended claims.

What is claimed is:

1. A method of detecting neonatal hemolysis without the requirement for laboratory analysis by automatically collecting neonatal end tidal breath for carbon monoxide analysis with minimal human intervention comprising the steps of:
   a) providing a syringe and plunger for collecting end tidal breath,
   b) connecting one end of a catheter to said syringe and placing another end of said catheter in the nostril of an infant,
   c) electronically determining rate of exhalation of breath,
   d) automatically incrementally withdrawing said plunger from said syringe and collecting end tidal breath,
   e) automatically controlling the withdrawal of said plunger in response to the exhalation of breath, said withdrawal being automatically delayed to near the end tidal breath as determined by exhalation rate, and
   f) analyzing said end tidal breath for carbon monoxide content as a measure of neonatal hemolysis.

* * * * *

UNITED STATES PATENT AND TRADEMARK OFFICE
CERTIFICATE OF CORRECTION

PATENT NO. : 5,383,469
DATED : January 24, 1995
INVENTOR(S) : HENDRIK K. VREMAN and DAVID K. STEVENSON It is certified that error appears in the above-indentified patent and that said Letters Patent is hereby corrected as shown below:

Column 1, line 6, after the title, insert the following paragraph:

--This invention was made with Government support under contracts HD14426 and HD27880 awarded by the National Institutes of Health. The Government has certain rights in this invention.--

Signed and Sealed this

Sixteenth Day of May, 1995

Attest:

BRUCE LEHMAN

Attesting Officer    Commissioner of Patents and Trademarks